US006383515B2

(12) United States Patent
Sawyer et al.

(10) Patent No.: US 6,383,515 B2
(45) **Date of Patent: *May 7, 2002**

(54) SOLVENT SYSTEM FOR ENHANCING SOLUBILITY

(76) Inventors: MaryJean Sawyer, 420 Cardinal La., Bedminster, NJ (US) 07921; Anthony Efiong Ekpe, 16 Colgate Rd., Maplewood, NJ (US) 07040; Maw-Sheng Wu, 6 McVickers La., Mendham, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/322,819

(22) Filed: May 28, 1999

(51) Int. Cl.[7] .................................................. A61K 9/64

(52) U.S. Cl. ....................... 424/456; 424/451; 424/455; 514/772.2

(58) Field of Search ................................ 424/451, 455, 424/456

(56) References Cited

U.S. PATENT DOCUMENTS

| | | | | |
|---|---|---|---|---|
| 3,557,280 A | | 1/1971 | Weber et al. | 424/80 |
| 4,525,348 A | | 6/1985 | Arizono et al. | 424/81 |
| 4,690,823 A | | 9/1987 | Lohner et al. | 424/456 |
| 4,701,327 A | | 10/1987 | Henmi et al. | 424/455 |
| 4,708,834 A | | 11/1987 | Cohen et al. | 424/456 |
| 4,713,246 A | | 12/1987 | Begum et al. | 424/455 |
| 4,798,725 A | | 1/1989 | Patel | 424/456 |
| 4,868,207 A | * | 9/1989 | Shi-jie | 514/464 |
| 5,071,643 A | | 12/1991 | Yu et al. | 514/570 |
| 5,360,615 A | | 11/1994 | Yu et al. | 424/455 |
| 5,505,961 A | | 4/1996 | Shelley et al. | 424/451 |

* cited by examiner

*Primary Examiner*—Thurman K. Page
*Assistant Examiner*—Liliana Dinola-Baron
(74) *Attorney, Agent, or Firm*—John S. Child, Jr.

(57) ABSTRACT

A pharmaceutically acceptable solution with a medicament suitable for filling a soft gelatin capsule is made from a solvent. The solvent contains a polymer, such as polyethylene glycol, and an acid salt of a compound having 3 or more carbon atoms, and a salt such as sodium propionate. The solvent may optionally contain a cosolvent, such as dimethyl isosorbide. The medicament may preferably comprise an analgesic such as aspirin or naproxen.

13 Claims, No Drawings

SOLVENT SYSTEM FOR ENHANCING SOLUBILITY

BACKGROUND OF THE INVENTION

1. Field of the Invention

The invention relates to medicinal solutions suitable for encapsulation in soft gelatin capsules. More particularly, the invention relates to pharmaceutically acceptable solvent systems capable of producing a highly concentrated solution of a medicament, such as acetaminophen or naproxen, for use in a soft gelatin capsule.

2. Description of Related Art

Soft gelatin capsules or "softgels" are, as their name implies, gelatin capsules that are softer than conventional caplets, capsules or tablets. They are commonly used to encapsulate liquids containing an active ingredient or ingredients. Softgels are used to contain consumables, such as vitamins or pharmaceuticals, including products in the over-the-counter market. Softgels are also used in many other industries, and have been used to encapsulate such diverse substances as industrial adhesives and bath oils.

In the pharmaceutical industry, softgels provide many benefits over conventional liquid and solid administration vehicles. They dissolve in the stomach faster than compressed tablets. Tablets must dissolve in the stomach or intestines and so generally retard the speed of onset of a medicament administered in a tablet form. Tablets are also generally unsuited for administration of liquids. Hard gelatin or starch-based capsules may be used for liquid or solid delivery systems. But, capsules are generally not appropriate for liquids because the hard gelatin or starch capsules may be either softened or entirely dissolved by a liquid medicament. In addition, some air is usually trapped in a hard gelatin capsule, where a liquid "fill" is put into the capsule. This air bubble can affect the active ingredients and detract from the appearance of the product. Softgels are better than direct liquid administration because liquids spill, and some medicaments may have unacceptable or unpleasant taste even with taste masking agents. Softgels, on the other hand, dissolve rapidly in the stomach and the body quickly absorbs the liquid interior of the softgel, so softgels offer an attractive means of administering a medicament.

Not all liquids may be enclosed in a softgel. Liquids containing more than about 20% water by weight are generally not enclosed in softgels, because the water tends to dissolve the gelatin shell. Propylene glycol, glycerin, low molecular weight alcohols, ketones, acids, amines, and esters all tend to degrade or dissolve the softgel layer gelatin to some extent. Thus, formulations that are enclosed in a softgel cannot contain significant amounts of many well-known solvents.

Softgels are also somewhat sensitive to pH, and generally require a pH in the encapsulated liquid from about 2.5 to about 7.5. Highly acidic liquids may hydrolyze the gelatin, resulting in leaks, while basic liquids may tan the gelatin, resulting in decreased solubility of the gelatin shell.

Pharmaceutical liquids are usually enclosed in softgels as either viscous solutions or suspensions. Suspensions are pharmaceutically less desirable because they can settle during manufacture, which leads to a less uniform product. If a suspension is used, the solid particles in a suspension should be smaller than about 80 mesh, otherwise the softgel filling equipment might not function optimally.

Suitable softgel solutions, however, can be difficult to achieve. The walls of a softgel are thicker than the walls of a caplet or a hard gelatin capsule. The softgel should be small enough for patient acceptance. The thickness of the walls reduces the available space for the medicament. But, the softgel must contain sufficient quantities of the medicament to be effective. One approach, of course, is simply to require the consumer to swallow more than one softgel to achieve any adequate dose of the medicament. Consumers, however, prefer taking one or two softgels, tablets or capsules and resist taking more than three.

The solution in the softgel must thus be highly concentrated. High concentration levels, though, strain the ability of conventional solvent systems to dissolve a sufficient quantity of the pharmaceutical agent. A strong solvent, on the other hand, can degrade the gelatin coating. So, a frequent problem in softgel applications is dissolving the active ingredient or ingredients in a sufficiently small amount of solvent to provide a potent dose of the medicament in the softgel. Solvent systems must be used that are tailored to the specific needs of a specific medicament or blend of medicaments. For example, U.S. Pat. No. 3,557,280 to Weber et al., issued January 1971, used a magnesium salt, polyvinylpyrrolidone and water to dissolve oxytetracycline for injection or oral liquid administration. U.S. Pat. No. 5,071,643 to Yu et al., issued Dec. 10, 1991 and U.S. Pat. No. 5,360,615 also to Yu et al., issued Nov. 1, 1994, used polyethylene glycol and an acid or a base to dissolve ibuprofen, naproxen, indomethacin or acetaminophen (among others).

Another solvent system, found in U.S. Pat. No. 5,505,961 to Shelley et al., issued Apr. 9, 1996, used polyethylene glycol and sodium or potassium acetate to enhance the solubility of acetaminophen.

Despite these efforts, there is still a strong need in the art for solvent systems that can dissolve large amounts of a medicament, especially without the addition of large amounts of an acid or base.

SUMMARY OF THE INVENTION

It is an object of the present invention to provide a solvent system capable of producing a highly concentrated solution of a pharmaceutical agent suitable for encapsulation into a softgel of suitable size without neutralizing large amounts of the agent.

It is a further object of the present invention to create such a solvent system that can be safely consumed by human beings.

It is a further object of the present invention to use such a solvent system to create a highly concentrated solution of a medicament, like acetaminophen or naproxen, suitable for use as a fill in a softgel. About a one ml softgel should encapsulate about 325 mg of acetaminophen or about 220 mg of naproxen.

It is a further object of the present invention to create a solvent system for enhancing the solubility of medicaments, including such over-the-counter medicaments as pain relievers and cold remedies.

It is an advantage of the invention that one of the ingredients in the solvent system may itself be an antifungal agent, thereby increasing the safety of the solvent system during storage and handling.

Additional objects and advantages of the invention will be set forth in part in the description that follows, and in part will be obvious from the description.

To achieve the foregoing objects and in accordance with the purpose of the invention, as embodied and broadly described herein, the invention provides a pharmaceutically acceptable solution comprising a medicament and a solvent system. The solvent system comprises a low molecular weight polymer and a salt of an organic acid containing at least three carbon atoms.

To further achieve the foregoing objects and in accordance with the purpose of the invention, as embodied and broadly described herein, the invention provides a method for dissolving a large amount of a medicament in a small amount of solvent. The solvent comprises a low molecular weight polymer and a salt of an organic acid containing at least three carbon atoms.

DESCRIPTION OF THE PREFERRED EMBODIMENTS

We will now describe the preferred embodiments of the invention.

The formulation of the invention comprises three types of systems: (a) a solvent system; (b) a solvent system and a medicament; and (c) a solvent system, at least one medicament dissolved in the solvent system, and a softgel surrounding the medicament and solvent system.

The solvent system of the invention comprises a low molecular weight polymeric material and a salt of an organic acid containing at least three carbon atoms. The system may also contain additional ingredients as set out below.

One part of the solvent system of the invention is a low molecular weight polymeric material. As used herein, "a low molecular weight" polymer is any polymer that is liquid or semi-solid at about room temperature and pressure when combined in a solvent system or any polymer that can dissolve in a limited amount of water to form a solvent system. The particular identity of the polymeric entity selected as the solvent will guide one skilled in the art to the appropriate molecular weight for the polymer. Since the polymer will be ingested into the human body, it must be safe and nontoxic (at least when used in the amounts contemplated herein). While the polymer need not be organoleptically pleasing, the polymer preferably does not cause any adverse side reactions or other detrimental effect on humans upon ingestion.

Linear or branched polymers, of course, generally do not have a single molecular weight. Rather, each strand in a polymer sample will have a different length and the "molecular weight" of a polymer sample will be the average molecular weight of the strands.

Acceptable polymers that may be used in the invention include polyalkylene glycols and polyvinyl pyrollidones and analogs thereof, including various copolymers, polymer blends and modified polymers thereof. The polymers of the invention may also include polymeric materials that are not ordinarily thought of as polymers, such as glycerin and propylene glycol. The preferred polymers of the invention are polyols, such as glycerin, propylene glycol and polyalkylene glycols. More preferred are polyethylene glycols and polypropylene glycols. More preferably, the polyethylene glycols of the invention have a molecular weight of less than about 1500, since polyethylene glycol 1500 is reported to be solid at room temperature. (Molecular weights of about 1500 or above are not excluded from the invention to the extent that the polymer may be semi-solid, liquid or soluble in limited amounts of water.) Most preferably, the molecular weight of the polyethylene oxide is from about 400 to about 600 daltons, and the most preferred embodiment of the invention uses polyethylene glycol having a molecular weight of about 600. The solvent may comprise mixtures of materials as well. For example, a polyethylene glycol having a molecular weight of about 600 may be obtained by using PEG 600 or about a 50/50 mixture of PEG 400 and PEG 800.

The polymeric material preferably comprises from about 10% by weight to about 70% by weight of the solution of the invention. More preferably, the polymeric material comprises from about 15% by weight to about 65% by weight of the solution and even more preferably, the polymeric material comprises from about 20% by weight to about 55% by weight of the solution. Most preferably, the polymeric material comprises from about 30% by weight to about 50% by weight of the solution of the invention. When blends of the polymers are used as a solvent, it is preferable, but not critical, that one species of polymer predominates. Thus, in one preferred embodiment of the invention, the solvent system comprises from about 15% to about 65% by weight polyethylene glycol 600 and from 0% to about 5% by weight of (and more preferably from 0% to about 2% by weight) propylene glycol.

In addition to the polymeric material, the invention also comprises a salt of an organic acid containing at least three carbon atoms. The salt helps to ionize the medicament, especially where the medicament is capable of forming a zwitterion, without relying on strong acids or bases.

Preferred cations for the salt are monovalent and divalent cations that are nontoxic and acceptable for human consumption. These cations include, but are not limited to, sodium, potassium, and calcium ions. Alkali cations are preferred, and sodium is the most preferred cation.

The anion of the salt is an organic acid anion containing at least three carbon atoms. Acceptable acid anions include those capable of forming a nontoxic salt with any of the cations of the invention. Although the preferred acid anions are from saturated aliphatic acids having from three to six carbon atoms, other acids are not excluded from the scope of the invention. Aromatic acids, saturated acids having more than six carbon atoms, and unsaturated acids having more than three carbon atoms may be used, so long as the acid forms a nontoxic salt. More preferred acids include mono, di- and tri-carboxylic acids having three to six carbon atoms, including propionic acid, pyruvic acid, citric acid, and butanoic acid. Propionic acid is the most preferred because it has antifungal properties.

In a highly preferred embodiment of the invention, the salt is a sodium propionate salt that is added to the solution of the invention as a salt/water solution. Preferred concentrations of the salt solution are from about 40% by weight to a saturated solution of the salt in water.

The pH of this propionate solution may be adjusted by the addition of small amounts of propionic acid, usually no more than about 1–2% by weight of the propionate solution. So, the numbers in the examples may be slightly incorrect.

The salt may comprise from about 2% by weight to about 40% by weight of the solution of the invention. More preferably, the salt comprises from about 4% to about 35% by weight of the solution of the invention, and even more preferably, from about 4% by weight to about 25% by weight of the solution of the invention. Preferably the pH is adjusted in the salt/water solution to provide acceptable pH limits in the softgel.

The solvent system of the invention may also contain additional ingredients such as cosolvents, including dimethyl isosorbide, oils, including soybean oil, and water. The cosolvent may comprise from 0% by weight to about 30% by weight of the solution of the invention, and more preferably from about 5% by weight to about 20% by weight of the solution of the invention. Most preferably, the cosolvent is dimethyl isosorbide and comprises from about 5% by weight to about 10% by weight of the solution of the invention. Water may comprise from 0% by weight to about 25% by weight of the solution of the invention. Oils may comprise from 0% to about 20% by weight of the solution of the invention, and more preferably from 0% to about 15% by weight of the solution of the invention. In the examples that follow, water is added as part of a sodium propionate solution that is added to the solvent system. In some of these examples, the reported amounts in grams were calculated from the density and volume of the propionate solution added.

The medicament of the invention may be any medicament, but the softgels of the invention are of primary benefit in human consumption, so the medicaments of the invention are preferably those intended for use by humans. Preferred medicaments are those used in over-the-counter treatments of coughs, colds and other common ailments. Thus, highly preferred medicaments include pain relievers, such as aspirin, acetaminophen, naproxen, ibuprofen and other nonsteroidal anti-inflammatory drugs, as well as the so-called "Cox-2" inhibitors. Other highly preferred medicaments include, but are not limited to, cough suppressants, such as dextromethorphan, decongestants, such as pseudoephedrine, and antihistamines, such as chlorpheniramine and doxylamine compounds. Medicaments that form zwitterions when dissolved with the salts of the invention are most highly preferred.

The total amount of medicaments of the invention may comprise from about 25% by weight of the solution up to the amount that will form a fully saturated solution, usually up to about 70% by weight of the solution. Preferably, however, the medicaments comprise from about 30% by weight to about 55% by weight of the solution of the invention. Of course, dosage levels will be adjusted to reflect the needs of the patient, not the needs of the solvent.

Consumer preference suggests that clear or at least translucent solutions should be used in softgels. The solvent system of the present invention may be adjusted to provide such a clear solution acceptable to consumers. In the examples that follow, many of the solutions have a color. The color may be significantly reduced by carrying out the solution process in the absence of oxygen. While the examples used a nitrogen blanket, the solution was exposed to air while various materials were added, which affected the final color of the solution.

The medicament should remain in solution to achieve the benefits of the invention, and the solution should remain stable over time and under conditions normally encountered in consumer applications. The solution disclosed in the present invention has been found stable and robust in a number of tests. For instance, the solution has been placed "on the shelf" at room temperature for extended periods of time, and has remained clear and stable, without precipitation of the medicament. Moreover, the solution has been subjected to alternating refrigeration and room temperature conditions, and the medicament has not crystallized, and has remained stable and clear.

The solution has been placed in softgels successfully, at least on an experimental level. The gelatin in a softgel may be any known on the art. Suitable results have been achieved with Type A gelatin, bloom strength 150. Hydrophilic softgels are preferred.

The selection of ingredients to be used in the solvent system will, of course, depend on the medicament to be administered. Different medicaments, such as naproxen, aspirin and acetaminophen, have different chemical structures and different affinities for various solvent combinations. Highly concentrated solutions of medicaments, such as aspirin and naproxen, require a solvent system tailored to the specific needs of the medicament.

The solution of the invention may be prepared through mixing of the ingredients. This mixing takes place preferably at an elevated temperature and with applied shear. While the applied shear does not necessarily allow for greater solubility of any ingredient, it appears to provide better stability of the solution during handling and storage. Preferably, the solvent is prepared first and the medicament is then added to the solvent. The salt is then also added slowly to help dissolve the medicament. It appears that if the salt is added too quickly, ionization of the medicament does not take place and the material does not form a successful solution. The process may be carried out in whole or in part in a nitrogen atmosphere if the presence of oxygen might discolor or otherwise damage any ingredient in the solution.

Preferred embodiments of the invention have been prepared as described in the examples below. A solution of polyethylene glycol 600 and, optionally, dimethyl isosorbide is prepared in a glass flask, and is stirred at about 250 rpm, and heated to about 50° C. (An acceptable solution may be prepared without dimethyl isosorbide.) The flask may then be deaerated with nitrogen. Acetaminophen or another medicament is added and a stopper is used to cover the flask. Next, the sodium propionate solution is added dropwise, using a metered flow control device. The formulation is again blanketed with nitrogen and then stirred at about 300 rpm with heat until clear, which usually requires from about 30 to about 120 minutes. Another preferred embodiment incorporates shear to help the materials to blend more quickly and thoroughly.

EXAMPLES

The following examples are intended to demonstrate some embodiments of the invention without limiting the scope or spirit of the invention. Due to rounding, total percentages for some of the formulations described below do not equal 100%. In some examples the amount of added propionate solution was recorded in mls. of solution added. This recorded number was converted to grams using an approximate density of 1.17 to 1.18

Example 1

A solution was prepared having the formulation set forth in Table 1 as follows. The polyethylene glycol, dimethyl isosorbide and soybean oil were combined in a 250 ml flask. This mixture was heated to about 45° C. and stirred at about 250 rpm. The flask was blanketed with nitrogen gas, and acetaminophen was added as quickly as possible to reduce discoloration of the solution. A solution containing the water and the sodium propionate was slowly added to the mixture. A clear, brown colored solution was obtained. Due to rounding, the percentages do not add up to 100%.

TABLE 1

Formulation of Example 1

| Ingredient | Amount | Weight Percent (%) |
|---|---|---|
| Polyethylene glycol 600 | 25 g | 25% |
| Dimethyl isosorbide | 15 g | 15% |
| Water | 5 g | 5% |
| Soybean oil | 16 g | 16% |

TABLE 1-continued

Formulation of Example 1

| Ingredient | Amount | Weight Percent (%) |
|---|---|---|
| Sodium propionate | 5.5 g | 5.5% |
| Acetaminophen | 33 g | 33% |
| Chlorpheniramine | 0 g | 0% |
| Pseudoephedrine | 0 g | 0% |
| Dextromethorphan | 0 g | 0% |
| Doxylamine succinate | 0 g | 0% |
| Propylene glycol | 0 g | 0% |

Example 2

A formulation was prepared with the ingredients set forth in Table 2. The polyethylene glycol and dimethyl isosorbide were mixed, and a slurry of the sodium propionate and water was added to the mixture. This mixture was heated to 45° C. and stirred to dissolve the slurry. The acetaminophen was added in 5-gram portions, and complete solubility was obtained, providing a clear, light pink colored solution. Although some crystallization was observed upon cooling, only minimal precipitation had been observed after storage for ten days at room temperature.

TABLE 2

Formulation of Example 2

| Ingredient | Amount | Weight Percent (%) |
|---|---|---|
| Polyethylene glycol 600 | 35 g | 43% |
| Dimethyl isosorbide | 5 g | 6% |
| Water | 4 g | 5% |
| Soybean oil | 0 g | 0% |
| Sodium propionate | 5 g | 6% |
| Acetaminophen | 32.5 g | 40% |
| Chlorpheniramine | 0 g | 0% |
| Pseudoephedrine | 0 g | 0% |
| Dextromethorphan | 0 g | 0% |
| Doxylamine succinate | 0 g | 0% |
| Propylene glycol | 0 g | 0% |

Example 3

A formulation was prepared with the ingredients set forth in Table 3. Polyethylene glycol 600 and dimethyl isosorbide were combined, heated to 45° C., and stirred. The sodium propionate was mixed with the water to form a solution and added to the solvents. Acetaminophen was added, and a clear, pink colored solution was obtained.

TABLE 3

Formulation of Example 3

| Ingredient | Amount | Weight Percent (%) |
|---|---|---|
| Polyethylene glycol 600 | 21 g | 20% |
| Dimethyl isosorbide | 6 g | 6% |
| Water | 15 g | 14% |
| Soybean oil | 0 g | 0% |
| Sodium propionate | 12 g | 11% |
| Acetaminophen | 51 g | 49% |
| Chlorpheniramine | 0 g | 0% |
| Pseudoephedrine | 0 g | 0% |
| Dextromethorphan | 0 g | 0% |
| Doxylamine succinate | 0 g | 0% |
| Propylene glycol | 0 g | 0% |

Example 4

A formulation was prepared with the ingredients set forth in Table 4. A solution of the sodium propionate in the water was prepared by mixing at room temperature until dissolved. The polyethylene glycol and the dimethyl isosorbide were put into a 125-ml glass-stoppered Erlenmeyer flask. The mixture was stirred and heated and blanketed with nitrogen. The acetaminophen was then added, and the sodium propionate solution was then added. A clear, pink colored solution was obtained. After placing the solution in a freezer for four hours the solution was removed and allowed to return to room temperature. No crystallization was observed.

TABLE 4

Formulation of Example 4

| Ingredient | Amount | Weight Percent (%) |
|---|---|---|
| Polyethylene glycol 600 | 39.6 g | 40% |
| Dimethyl isosorbide | 6.2 g | 6% |
| Water | 10 g | 10% |
| Soybean oil | 0 g | 0% |
| Sodium propionate | 7.9 g | 8% |
| Acetaminophen | 33 g | 34% |
| Chlorpheniramine | 0 g | 0% |
| Pseudoephedrine | 0 g | 0% |
| Dextromethorphan | 0 g | 0% |
| Doxylamine succinate | 0 g | 0% |
| Propylene glycol | 1.8 g | 2% |

Example 5

A formulation was prepared with the ingredients set forth in Table 5. A sodium propionate solution was prepared by dissolving 40 grams of sodium propionate in 50 mls of water. Polyethylene glycol and dimethyl isosorbide were then placed in a 250-ml distillation flask, stirred and heated. The acetaminophen was then added and nitrogen was blown into the stopper of the flask to keep oxygen away from the solution. 20–21 ml of the propionate solution were then added to the flask and stirring continued until a clear, pink colored solution was obtained. This solution was blanketed with nitrogen, stoppered and frozen for 16 hours. The solution then returned to room temperature, and slight crystal formation was observed on the surface of the solution.

TABLE 5

Formulation of Example 5

| Ingredient | Amount | Weight Percent (%) |
|---|---|---|
| Polyethylene glycol 600 | 42.4 g | 39% |
| Dimethyl isosorbide | 9.94 g | 9% |
| Water | 13.7 g | 12% |
| Soybean oil | 0 g | 0% |
| Sodium propionate | 11 g | 10% |
| Acetaminophen | 32.7 g | 30% |
| Chlorpheniramine | 0 g | 0% |
| Pseudoephedrine | 0 g | 0% |
| Dextromethorphan | 0 g | 0% |
| Doxylamine succinate | 0 g | 0% |
| Propylene glycol | 0 g | 0% |

Example 6

A formulation was prepared with the ingredients set forth in Table 6. A sodium propionate solution was prepared by dissolving 40 grams of sodium propionate in 50 mls of water. Polyethylene glycol and dimethyl isosorbide were then placed in a 250-ml distillation flask, stirred and heated. The acetaminophen was then added and nitrogen was blown into the stopper of the flask to keep oxygen away from the solution. 20–21 ml of the propionate solution were then added to the flask and stirring continued until a clear, pink colored solution was obtained. This solution was blanketed with nitrogen, stoppered and frozen for 16 hours. The solution was then returned to room temperature, and slight crystal formation was observed on the bottom of the solution.

TABLE 6

Formulation of Example 6

| Ingredient | Amount | Weight Percent (%) |
|---|---|---|
| Polyethylene glycol 600 | 29.5 g | 27% |
| Dimethyl isosorbide | 19.9 g | 19% |
| Water | 13.7 g | 13% |
| Soybean oil | 0 g | 0% |
| Sodium propionate | 11 g | 10% |
| Acetaminophen | 33.2 g | 31% |
| Chlorpheniramine | 0 g | 0% |
| Pseudoephedrine | 0 g | 0% |
| Dextromethorphan | 0 g | 0% |
| Doxylamine succinate | 0 g | 0% |
| Propylene glycol | 0 g | 0% |

Example 7

A formulation was prepared with the ingredients set forth in Table 7. A sodium propionate solution was prepared by dissolving 40 grams of sodium propionate in 50 mls of water. Polyethylene glycol and dimethyl isosorbide were then placed in a 250-ml distillation flask, stirred and heated. The acetaminophen was then added and nitrogen was blown into the stopper of the flask to keep oxygen away from the solution. 20–21 ml of the propionate solution were then added to the flask and stirring continued until a clear, pink colored solution was obtained. This solution was blanketed with nitrogen, stoppered and frozen for 16 hours. The solution was then allowed to return to room temperature, and no crystal formation was observed.

TABLE 7

Formulation of Example 7

| Ingredient | Amount | Weight Percent (%) |
|---|---|---|
| Polyethylene glycol 600 | 27.2 g | 24% |
| Dimethyl isosorbide | 28.8 g | 25% |
| Water | 13.7 g | 12% |
| Soybean oil | 0 g | 0% |
| Sodium propionate | 11 g | 10% |
| Acetaminophen | 33 g | 29% |
| Chlorpheniramine | 0 g | 0% |
| Pseudoephedrine | 0 g | 0% |
| Dextromethorphan | 0 g | 0% |
| Doxylamine succinate | 0 g | 0% |
| Propylene glycol | 0 g | 0% |

Example 8

A formulation was prepared with the ingredients set forth in Table 8. The polyethylene glycol and the dimethyl isosorbide were placed into a 250-ml distillation flask, heated to 50° C. and stirred. The chlorpheniramine was added and stirring continued until it was completely dissolved. The acetaminophen was then added and the flask was blanketed with nitrogen. 20 ml of a sodium propionate solution (600 g sodium propionate in 800 ml water) was added to the flask and the nitrogen blanket was reapplied. Stirring continued for about two hours. Pseudoephedrine was then added and stirring continued overnight. A cloudy, light yellow solution was obtained. An additional 5 ml of the sodium propionate solution was added, the solution was reheated and stirring continued until a clear, light orange colored solution was obtained.

TABLE 8

Formulation of Example 8

| Ingredient | Amount | Weight Percent (%) |
|---|---|---|
| Polyethylene glycol 600 | 38.2 g | 34% |
| Dimethyl isosorbide | 12.9 g | 11% |
| Water | 15.1 g | 12% |
| Soybean oil | 0 g | 0% |
| Sodium propionate | 10.5 g | 9% |
| Acetaminophen | 37.6 g | 31% |
| Chlorpheniramine | 0.24 g | 0.2% |
| Pseudoephedrine | 3.2 g | 2.8% |
| Dextromethorphan | 0 g | 0% |
| Doxylamine succinate | 0 g | 0% |
| Propylene glycol | 0 g | 0% |

Example 9

A formulation was prepared with the ingredients set forth in Table 9. The polyethylene glycol was charged into a 250-ml distillation flask and heated to 50° C. and stirred. The acetaeminophen was added to the flask, and the flask was blanketed with nitrogen while stirring and heating continued. 30 mls of the sodium propionate solution were added, the nitrogen blanket was reapplied and stirring continued for two hours until a light pink solution was obtained. After the solution was kept in the freezer overnight and then placed in warm water some crystals appeared, so an additional 5 ml of the sodium propionate solution was added under heat and stirring to redissolve the crystals.

TABLE 9

Formulation of Example 9

| Ingredient | Amount | Weight Percent (%) |
|---|---|---|
| Polyethylene glycol 600 | 50.1 g | 40% |
| Dimethyl isosorbide | 0 g | 0% |
| Water | 22.9 g | 18% |
| Soybean oil | 0 g | 0% |
| Sodium propionate | 18.4 g | 15% |
| Acetaminophen | 33.5 g | 27% |
| Chlorpheniramine | 0 g | 0% |
| Pseudoephedrine | 0 g | 0% |
| Dextromethorphan | 0 g | 0% |
| Doxylamine succinate | 0 g | 0% |
| Propylene glycol | 0 g | 0% |

Example 10

A formulation was prepared using the ingredients set forth in Table 10. The PEG-600 was added to a tared, 250-ml glass-stoppered flask and blanketed with nitrogen. The PEG-600 was heated to about 60° C. with stirring. The acetaminophen was then added slowly and the mixture was blanketed with nitrogen. Sodium propionate: solution was prepared by dissolving 500 grams of sodium propionate into 500 mls water. This solution was then added dropwise to the flask until a clear, yellow colored solution was obtained. The percentages do not add up to 100% due to rounding errors.

TABLE 10

| Formulation of Example 10 | | |
|---|---|---|
| Ingredient | Amount | Weight Percent (%) |
| Polyethylene glycol 600 | 54.8 g | 54% |
| Dimethyl isosorbide | 0 | 0% |
| Water | 7.1 g | 7% |
| Soybean oil | 0 | 0% |
| Sodium propionate | 7.1 g | 7% |
| Acetaminophen | 33.4 g | 33% |
| Chlorpheniramine | 0 | 0% |
| Pseudoephedrine | 0 | 0% |
| Dextromethorphan | 0 | 0% |
| Doxylamine succinate | 0 | 0% |
| Propylene glycol | 0 | 0% |

Example 11

A formulation was prepared with the ingredients set forth in Table 11. A flask was charged with PEG-600 and heated to about 55° C. The PEG was blanketed with nitrogen and stirred with an impeller blade at about 200 rpm. Acetaminophen was slowly added over a 25-minute period to form a fully wetted white slurry. A 1:1 by weight sodium propionate solution (in water) was added to the mix dropwise at about 4 to 5 drops per minute while the slurry was maintained under nitrogen and while stirring continued at about 200 rpm. The temperature of the PEG was maintained at about 48° to about 55° C. A clear, pink colored solution was obtained. The pH of the sodium propionate solution was adjusted from 9.1 to 7.1 by the addition of a small amount of undiluted propionic acid. The percentages do not add up to 100% due to rounding errors.

TABLE 11

| Formulation of Example 11 | | |
|---|---|---|
| Ingredient | Amount | Weight Percent (%) |
| Polyethylene glycol 600 | 262 g | 51% |
| Dimethyl isosorbide | 0 g | 0% |
| Water | 38.4 g | 7.5% |
| Soybean oil | 0 g | 0% |
| Sodium propionate solution | 38.4 g | 7.5% |
| Acetaminophen | 170.5 g | 33% |
| Chlorpheniramine | 0 g | 0% |
| Pseudoephedrine | 0 g | 0% |
| Dextromethorphan | 0 g | 0% |
| Doxylamine succinate | 0 g | 0% |
| Propylene glycol | 0 g | 0% |

Example 12

A formulation was prepared with the ingredients set forth in Table 12. The PEG-600 was added to 250-ml glass-stoppered distillation flask. A stir bar was added to the flask, and the PEG was heated to about 60° C. with stirring. The pseudoephedrine was mixed with 1.5 ml water and dissolved in the PEG. The acetaminophen was then added slowly, and the temperature was lowered to 50–55° C. The flask was blanketed with nitrogen. A 1:1 by weight solution of sodium propionate in water was prepared. About 16 ml of the sodium propionate solution was added slowly to the flask over two hours. A clear, pink/orange colored solution was obtained. An additional 5 ml of the sodium propionate solution was added after 24 hours to redissolve some crystals that had settled out overnight. The pH of the sodium propionate solution had been adjusted to 6.8 by the addition of undiluted propionic acid. Due to rounding errors, the percentages do not add up to 100%/

TABLE 12

| Formulation of Example 12 | | |
|---|---|---|
| Ingredient | Amount | Weight Percent (%) |
| Polyethylene glycol 600 | 51 g | 45% |
| Dimethyl isosorbide | 0 g | 0% |
| Water | 0 g | 11% |
| Soybean oil | 0 g | 0% |
| Sodium propionate | 12.4 g | 11% |
| Acetaminophen | 35 g | 31% |
| Chlorpheniramine | 0 g | 0% |
| Pseudoephedrine | 3 g | 3% |
| Dextromethorphan | 0 g | 0% |
| Doxylamine succinate | 0 g | 0% |
| Propylene glycol | 0 g | 0% |

Example 13

A formulation was prepared with the ingredients set forth in Table 13. The PEG-600 was added to 250-ml glass-stoppered distillation flask. A stir bar was added to the flask, and the PEG was heated to about 60° C. with stirring. The pseudoephedrine was mixed with 1.5 ml water and dissolved in the PEG. The acetaminophen was then added slowly, and the temperature was lowered to 50–55° C. The flask was blanketed with nitrogen. The 1:1 by weight sodium propionate solution was added slowly over two hours. A clear, pink colored solution was obtained. The pH of the sodium propionate solution was adjusted to 6.8 by the addition of undiluted propionic acid. The percentages do not add up to 100% due to rounding errors.

TABLE 13

| Formulation of Example 13 | | |
|---|---|---|
| Ingredient | Amount | Weight Percent (%) |
| Polyethylene glycol 600 | 50 g | 48% |
| Dimethyl isosorbide | 0 g | 0% |
| Water | 9.2 g | 9% |
| Soybean oil | 0 g | 0% |
| Sodium propionate | 7.7 g | 7% |
| Acetaminophen | 34 g | 33% |
| Chlorpheniramine | 0.25 g | 0.2% |
| Pseudoephedrine | 3 g | 3% |
| Dextromethorphan | 0 g | 0% |
| Doxylamine succinate | 0 g | 0% |
| Propylene glycol | 0 g | 0% |

Example 14

A formulation was prepared with the ingredients set forth in Table 14. The PEG-600 was added to 250-ml glass-stoppered distillation flask. A stir bar was added to the flask, and the PEG was heated to about 60° C. with stirring. The pseudoephedrine was mixed with 1.5 ml water and dissolved in the PEG. The acetaminophen was then added slowly, and the temperature was lowered to 50–55° C. The flask was blanketed with nitrogen. The 1:1 by weight sodium propionate solution was added slowly over about one hour. A clear, pink colored solution was obtained. The pH of the sodium propionate solution was adjusted to 6.8 by the addition of undiluted propionic acid. The percentages do not add up to 100% due to rounding errors.

TABLE 14

Formulation of Example 14

| Ingredient | Amount | Weight Percent (%) |
| --- | --- | --- |
| Polyethylene glycol 600 | 57 g | 42.9% |
| Dimethyl isosorbide | 0 g | 0% |
| Water | 12.7 g | 10.6% |
| Soybean oil | 0 g | 0% |
| Sodium propionate solution | 11.2 g | 9.4% |
| Acetaminophen | 35 g | 29.4% |
| Chlorpheniramine | 0 g | 0% |
| Pseudoephedrine | 3 g | 2.5% |
| Dextromethorphan | 0.15 g | 0.1% |
| Doxylamine succinate | 0 g | 0% |
| Propylene glycol | 0 g | 0% |

Example 15

A formulation was prepared with the ingredients set forth in Table 15. The PEG-600 was added to 250-ml glass-stoppered distillation flask. A stir bar was added to the flask, and the PEG was heated to about 60° C. with stirring. The pseudoephedrine was mixed with 1.5 ml water and dissolved in the PEG. The acetaminophen was then added slowly, and the temperature was lowered to 50–55° C. The flask was blanketed with nitrogen. The 1:1 by weight sodium propionate solution was added slowly over two hours. A clear, pink colored solution was obtained. The pH of the sodium propionate solution was adjusted to 6.8 by the addition of undiluted propionic acid. After 24 hours, some fine crystals appeared at the bottom of the flask. The percentages do not add up to 100% due to rounding errors.

TABLE 15

Formulation of Example 15

| Ingredient | Amount | Weight Percent (%) |
| --- | --- | --- |
| Polyethylene glycol 600 | 51 g | 42.8% |
| Dimethyl isosorbide | 0 g | 0% |
| Water | 15.1 g | 12.7% |
| Soybean oil | 0 g | 0% |
| Sodium propionate | 13.6 g | 11.4% |
| Acetaminophen | 36 g | 30.2% |
| Chlorpheniramine | 0.25 g | 0.2% |
| Pseudoephedrine | 3 g | 2.5% |
| Dextromethorphan | 0.16 g | 0.1% |
| Doxylamine succinate | 0 g | 0% |
| Propylene glycol | 0 g | 0% |

Example 16

A formulation was prepared with the ingredients set forth in Table 16. The PEG-600 was added to 250-ml glass-stoppered distillation flask. A stir bar was added to the flask, and the PEG was heated to about 60° C. with stirring. The pseudoephedrine was mixed with 1.5 ml water and dissolved in the PEG. The acetaminophen was then added slowly, and the temperature was lowered to 50–55° C. The flask was blanketed with nitrogen. 23 ml of a 1:1 by weight sodium propionate solution was added slowly over two hours. A clear, light orange colored solution was obtained. The pH of the sodium propionate solution was adjusted to 6.8 by the addition of undiluted propionic acid. After 24 hours, some crystal had appeared on the bottom of the flask. The solution we reheated to 55° C. with stirring and an additional 4 ml of the sodium propionate solution were added. The percentages do not add up to 100% due to rounding errors.

TABLE 16

Formulation of Example 16

| Ingredient | Amount | Weight Percent (%) |
| --- | --- | --- |
| Polyethylene glycol 600 | 50 g | 40.6% |
| Dimethyl isosorbide | 0 g | 0% |
| Water | 017.4 g | 14.1% |
| Soybean oil | 0 g | 0% |
| Sodium propionate | 15.9 g | 12.9% |
| Acetaminophen | 36 g | 29.2% |
| Chlorpheniramine | 0 g | 0% |
| Pseudoephedrine | 3 g | 2.4% |
| Dextromethorphan | 0.16 g | 0.1% |
| Doxylamine succinate | 0.72 g | 0.6% |
| Propylene glycol | 0 g | 0% |

Example 17

A formulation was prepared with the ingredients set forth in Table 17. The ingredients were mixed and the sample was heated in a steam bath and swirled until dissolved. The potassium hydroxide was added as a solution of 6.8 g KOH in 100 mls of water. The sodium propionate was added as a solution of 500 g sodium propionate in 700 mls of water. A clear solution was obtained.

TABLE 17

Formulation of Example 17

| Ingredient | Amount | Weight Percent (%) |
| --- | --- | --- |
| Naproxen sodium | 3.0033 g | 21.67 |
| Polyethylene Glycol 300 | 10.0332 g | 72.40 |
| Potassium hydroxide | 6.66 mg | 0.05 |
| Sodium propionate | 0.8153 g | 5.88 |

In each of the above examples, the solutions obtained were stable, and the acetaminophen did not precipitate. Also, in each of the above examples, we observed no evidence of acetaminophen degradation. Assay values showed greater than 98% recovery after ten weeks stored at room temperature under nitrogen.

Several of the solutions of the examples have been successfully incorporated into soft gelatin capsules using techniques well known in the art.

The purpose of the above description is to illustrate some embodiments of the invention without implying a limitation. It will be apparent to those skilled in the art that various modifications and variations may be made in the apparatus or procedure of the invention without departing from the scope or spirit of the invention.

We claim:

1. A pharmaceutically acceptable solution comprising between about 49% and about 70% of a medicament comprising acetaminophen and a solvent system wherein said solvent system comprises a low molecular weight polymeric material and a salt of an organic acid containing at least three carbon atoms.

2. The solution of claim 1 wherein said polymeric material is selected from the group consisting of polymers and copolymers of ethylene glycol.

3. The solution of claim 1, wherein said polymeric material has an average molecular weight of less than 1,500 daltons.

4. The solution of claim 1, further comprising a cosolvent.

5. A method of making a solution comprising about 49% to about 70% of a medicament comprising acetaminophen, said method comprising the steps of (a) preparing a solvent comprising a low molecular weight polymeric material; (b) adding a medicament to said solvent system to form a solution; and (c) blending a salt of an organic acid containing at least three carbon atoms with said polymeric material to form a solvent system.

6. The method of claim 5, further comprising the step of heating at least one of said solvent, said solvent system or said solution.

7. The solution of claim 1, wherein the salt of the organic acid comprises from about 4% by weight to about 25% by weight of the solution.

8. The solution of claim 1, wherein the cation of the salt of the organic acid containing at least three carbon atoms is selected from the group consisting of sodium, potassium and calcium.

9. The solution of claim 1, wherein the anion of the salt of the organic acid containing at least three carbon atoms comprises acid anions capable of forming a nontoxic salt with the salt's cation.

10. The solution of claim 1, wherein the anion of the salt of the organic acid containing at least three carbon atoms is selected from the group consisting of mono- di- and tricarboxylic acids having three to six carbon atoms.

11. The solution of claim 4, wherein the cosolvent comprises from about 5% by weight to about 20% by weight of the solution.

12. The method set forth in claim 5, wherein the step of blending the salt is carried out slowly to help dissolve the medicament.

13. The method set forth in claim 5, wherein the salt is added in the form of a sodium propionate salt/water solution wherein the salt is present in a concentration of from about 40% by weight to a saturated solution of the salt in water.

* * * * *